(12) United States Patent
Moavenian

(10) Patent No.: US 11,400,120 B2
(45) Date of Patent: Aug. 2, 2022

(54) COMPOSITION COMPRISING COLLAGEN AND HONEY

(71) Applicant: WELLAND MEDICAL LIMITED, West Sussex (GB)

(72) Inventor: Arash Moavenian, West Sussex (GB)

(73) Assignee: WELLAND MEDICAL LIMITED, Crawley (GB)

( * ) Notice: Subject to any disclaimer, the term of this patent is extended or adjusted under 35 U.S.C. 154(b) by 0 days.

(21) Appl. No.: 15/566,457

(22) PCT Filed: Apr. 15, 2015

(86) PCT No.: PCT/EP2015/058211
§ 371 (c)(1),
(2) Date: Oct. 13, 2017

(87) PCT Pub. No.: WO2016/165764
PCT Pub. Date: Oct. 20, 2016

(65) Prior Publication Data
US 2018/0085408 A1   Mar. 29, 2018

(51) Int. Cl.
| | | |
|---|---|---|
| *A61K 35/644* | (2015.01) | |
| *A61K 38/39* | (2006.01) | |
| *A61L 15/32* | (2006.01) | |
| *A61K 9/00* | (2006.01) | |
| *A61K 9/10* | (2006.01) | |
| *A61K 9/70* | (2006.01) | |
| *A61L 15/40* | (2006.01) | |
| *A61L 26/00* | (2006.01) | |
| *A61K 8/98* | (2006.01) | |
| *A61Q 19/00* | (2006.01) | |
| *A61K 8/65* | (2006.01) | |
| *A61K 8/04* | (2006.01) | |
| *A61K 45/06* | (2006.01) | |
| *A61L 27/24* | (2006.01) | |
| *A61L 27/36* | (2006.01) | |

(52) U.S. Cl.
CPC ............ *A61K 35/644* (2013.01); *A61K 8/044* (2013.01); *A61K 8/65* (2013.01); *A61K 8/988* (2013.01); *A61K 9/0014* (2013.01); *A61K 9/10* (2013.01); *A61K 9/7007* (2013.01); *A61K 38/39* (2013.01); *A61K 45/06* (2013.01); *A61L 15/325* (2013.01); *A61L 15/40* (2013.01); *A61L 26/0033* (2013.01); *A61L 26/0057* (2013.01); *A61L 27/24* (2013.01); *A61L 27/3604* (2013.01); *A61Q 19/00* (2013.01)

(58) Field of Classification Search
CPC .. A61K 2300/00; A61K 35/644; A61K 38/39; A61K 45/06; A61K 8/044; A61K 8/65; A61K 8/988; A61K 9/0014; A61K 9/10; A61K 9/7007; A61L 15/325; A61L 15/40; A61L 26/0033; A61L 26/0057; A61L 27/24; A61L 27/3604; A61Q 19/00
See application file for complete search history.

(56) References Cited

U.S. PATENT DOCUMENTS

| | | | | |
|---|---|---|---|---|
| 5,456,745 | A | * 10/1995 | Roreger | A61K 8/0208 106/140.1 |
| 2002/0168400 | A1 | * 11/2002 | Jain | A61L 15/22 424/445 |
| 2013/0245528 | A1 | * 9/2013 | Harrell | A61K 9/0014 602/50 |

FOREIGN PATENT DOCUMENTS

| | | | | |
|---|---|---|---|---|
| GB | 2 474 851 | A | 5/2011 | |
| GB | 2474851 | A * | 5/2011 | ............. A61L 15/40 |
| WO | WO 2008/049251 | A1 | 5/2008 | |
| WO | WO 2014/183770 | A1 | 11/2014 | |
| WO | WO-2014183770 | A1 * | 11/2014 | ......... A61L 26/0033 |
| WO | WO 2015/041835 | A1 | 3/2015 | |
| WO | WO 2015/041836 | A1 | 3/2015 | |

OTHER PUBLICATIONS

Database WPI, Week 199707, Thomson Scientific, London, GB; AN 1997-065923 & CN 1 077 630 A (Huaxin Biochemical Tech InstXicheng Dis) (Oct. 27, 1993).
Database WPI, Week 201308, Thomson Scientific, London, GB; AN 2012-G29388 & CN 102 451 143 A (Liu G) (May 16, 2012).
International Search Report in International Application No. PCT/EP2015/058211, dated Nov. 24, 2015.
International Preliminary Report on Patentability in International Application No. PCT/EP2015/058211, dated Oct. 17, 2017.

* cited by examiner

*Primary Examiner* — Michael B. Pallay
(74) *Attorney, Agent, or Firm* — Potter Anderson & Corroon LLP

(57) ABSTRACT

A composition comprising collagen and honey can be produced by addition of an aqueous solution of honey to an aqueous suspension of collagen. The composition is for use in medicine and particularly for use in the treatment of a wound. A method for treatment of a wound comprises administering the composition topically to the skin of a patient.

20 Claims, 3 Drawing Sheets

COMPOSITION COMPRISING COLLAGEN AND HONEY

The present invention relates to a composition comprising collagen and honey. The composition is for use in medicine and in particular for use in the treatment of wounds, preferably wounds inflicted by burns. The invention provides a method for treatment of a wound which comprises administering the composition topically to the skin of a patient.

BACKGROUND OF THE INVENTION

Collagen and honey are both naturally occurring materials which individually have had long standing history and recognition in promoting wound healing.

Collagen has found clinical success in applications spanning across dermal regeneration, cartilage repair, nerve repair and conjunctiva repair among others. In these applications collagen has served as a physical framework upon which cells involved in the natural healing process can adhere, migrate and proliferate across the wound site. Dressings containing collagen provide a source of collagen (as a sacrificial substrate) that can be degraded by high levels of matrix metalloproteinases (MMPs) present at wound sites, leaving endogenous native collagen to continue the process of normal wound healing.

Applied topically collagen acts as a haemostat and has been shown to stimulate growth of new tissue in a wound bed.

Collagen has roles in cellular differentiation, angiogenesis, cellular migration, induction of collagenases, wound contraction, platelet aggregation, induction of growth factors and cytokines through degradation products, cell surface receptors (integrins) in cell-signalling and induction.

The application of collagen discussed above has been focussed on regenerating tissue, whereas, in contrast, the use of honey has been used to reduce risk of infection while some components of the honey may well serve to promote healing.

Honey is known to have application in promoting healing of wounds. Specific commercially available grades of honey have been identified as exhibiting unique antibacterial and anti-inflammatory properties which can aid in wound healing. Relevant properties and mechanisms of action of honey are discussed below Antibacterial Action High sugar and low water content results in high affinity for water. This results in insufficient water available to support bacterial growth.

Honey is acidic—containing amino acids, organic acids and aromatic acids. Typically the pH of honey is about 4 and this is directly related to floral source of the honey. This acidic pH leads to inhibition of microbial growth because in general microbes prefer a neutral pH. A low pH has also been shown to increase oxygen diffusion and decrease protease activity. Proteases are known to have a role in breaking down unhealthy extracellular matric (ECM), but in elevated levels over prolonged periods they can destroy healthy ECM. Lower pH values also help to optimise conditions for fibroblast migration, proliferation and organisation of collagen, all of which contribute to wound healing.

The enzyme glucose oxidase is mixed with nectar during its collection by bees and although this enzyme is not active in the honey produced by the bees, it is activated upon dilution with wound fluid. It catalyses the oxidation of glucose to gluconic acid (which has a low pH) and hydrogen peroxide. These reaction products can confer antibacterial properties in some honeys. In Manuka honey the antibacterial properties have been attributed to methylglyoxal (MGO)—which originates from high levels of the compound dihydroxyacetone in the nectar of manuka flowers.

Anti-Inflammatory Action

Osmotic pressure generated by constituent sugars in honey attracts lymph out of cells which reduces oedema. This has an anti-inflammatory action because oedema has been shown to build pressure in tissues, thereby restricting blood flow and availability of oxygen and nutrients to cells.

Reduction of Malodour

Low pH inhibits bacterial growth, which would otherwise be expected to give rise to malodourous compounds like ammonia, amines and sulphur through metabolism of amino acids from decomposed tissue proteins. Any microbes present can feed on alternative sources of energy (glucose).

Osmotic Activity and Moist Wound Environment

Osmotic pressure of its constituent sugars attracts fluids/lymph from deeper tissues, bathing the wound site, bring up with it devitalised tissue and slough. The constant outflow of lymphatic fluid delivers plasminogen to wound site, helping to break down necrotic tissue (plasminogen is converted to plasmin which breaks the adhesion of necrotic tissue at the wound surface).

Wound care products have been developed based on collagen alone and on collagen in combination with other biological components. Similarly, products have been developed using honey (Manuka honey) alone as well as honey in combination with other materials such as alginates (calcium alginate and sodium alginate) and natural gelling agents. However, until now, there has been no known investigation into a composition comprising both collagen and honey and specific variants thereof, especially for application in wound healing.

Table 1 summarises the features of collagen and honey.

TABLE 1

| Property | Modality | Collagen | Honey | Collagen + Honey |
|---|---|---|---|---|
| Natural Source | — | ✓ | ✓ | ✓ |
| Non-toxic | — | ✓ | ✓ | ✓ |
| Safe | — | ✓ | ✓ | ✓ |
| Successful clinical history | — | ✓ | ✓ | ✓ |
| Commercial viability | — | ✓ | ✓ | ✓ |
| Extended wear time | Stability of components (cross-linking and weight fractions) and physical form of product may be adapted to application. | ✓ | ✓ | ✓ |
| Osmotic activity | High osmolarity cleanses and provides autolytic debridement in the wound by encouraging | ✓ | ✓ | ✓ |

TABLE 1-continued

| Property | Modality | Collagen | Honey | Collagen + Honey |
|---|---|---|---|---|
| | lymph fluid to rehydrate devitalised tissue and removing sloughy and necrotic tissue | | | |
| Antibacterial characteristics | Effective against a broad spectrum of wound pathogens through a distinctive heat stable antibacterial component - methylglyoxal (MGO) - the activity of which persists even in diluted form in contact with wound fluid. | X | ✓ | ✓ |
| pH modulation and anti-inflammatory effect | Chronic wounds suffer increased inflammation, giving rise to elevated levels of protease which degrade the extracellular matrix. Modulation - lowering - of wound pH which serves to: increase oxygen diffusion, decease damaging protease activity and improve wound healing. | X | ✓ | ✓ |
| Reduction in Malodour | Exudating and infected wounds carry malodour. Inhibition of anaerobic bacteria that have ability to ferment amino acids to malodorous organic amines. Some sugars may metabolised by bacteria into many odourless products. | X | ✓ | ✓ |
| Foam structure emulating extracellular matrix components | Biological scaffolds may be fabricated which provide an active framework upon which cells can adhere migrate and proliferate. | ✓ | X | ✓ |
| Provision of chemical cues for wound healing | Surface ligands on the dressing may provide chemical and biological cues which can direct and regulate cellular activity and promote healing | ✓ | X | ✓ |
| Splinting of wound site to prevent contraction | The scaffold may serve to prevent wound site contraction by a combination of cellular activity and mechanical splinting | ✓ | X | ✓ |

There is a need for further compositions which can be used to promote wound healing.

The present invention seeks to provide a composition for the treatment of wounds. In particular, the present invention seeks to provide a composition for the treatment of wounds inflicted by burns.

SUMMARY OF THE INVENTION

Remarkably, a novel method for production of a composition which comprises collagen and honey has been found. This has enabled a composition comprising both collagen and honey to be provided. Advantageously, the composition comprises natural components and this is more acceptable and more likely to be used by some patients than a medicament comprising synthetic components.

In accordance with the invention, in one aspect, there is provided a composition comprising collagen and honey.

In a further aspect, the invention provides a composition comprising collagen and honey for use in medicine.

In a further aspect, the invention provides a composition comprising collagen and honey for use in the treatment of a wound.

In a further aspect, the invention provides a method for treatment of a wound which comprises administering a composition according to the invention topically to the skin of a patient.

Preferably, a composition of the invention is applied to the wound for about 2 to about 7 days and reapplied thereafter depending on the severity of the wound until the wound is healed.

Preferably, the wound is a wound inflicted by a burn.

Preferably, the collagen is bovine collagen. Advantageously, bovine collagen is chemically similar to that of human collagen. This minimises risk of an host immune response and rejection by a patient.

Preferably, the honey is medical grade honey. More preferably, the honey is of Unique Manuka Factor (UMF) above+12. More preferably, the honey is of Unique Manuka Factor (UMF)+16 to UMF+20. More preferably, the honey has antibacterial and anti-inflammatory properties. An example is that of the *Leptospermum Scoparium* variety from the Manuka bush indigenous to New Zealand.

In one embodiment, the composition is in the form of an aqueous suspension.

Preferably, the suspension comprises an aqueous collagen suspension and an aqueous honey solution. Preferably, the suspension comprises collagen, honey, water and no other materials or substantially no other materials. Alternatively, the suspension includes one or more additional medicaments for the treatment of a wound. In this regard, one or more additional medicaments are preferably in suspension or in solution.

Preferably, the collagen suspension is a suspension of collagen in distilled water.

Preferably, the aqueous collagen suspension comprises about 0.1% to about 2.0% collagen by weight of the suspension. More preferably, the aqueous collagen suspension comprises about 0.5% to about 1% collagen by weight of the suspension.

Preferably, the honey solution is a solution of honey in distilled water or dilute acid.

Preferably, the suspension which comprises an aqueous collagen suspension and an aqueous honey solution comprises about 0.05% to about 5.0% honey by weight of the suspension. More preferably, the suspension which comprises an aqueous collagen suspension and an aqueous honey solution comprises about 0.1% honey by weight of the suspension.

In an alternative embodiment, the composition is in the form of a film or scaffold.

Preferably, the film or scaffold is prepared by drying the suspension which comprises collagen and honey.

Preferably, the film comprises collagen, honey, water and no other materials or substantially no other materials. Alternatively, the film includes one or more additional medicaments for the treatment of a wound. In this regard, one or more additional medicaments are preferably integral with the film.

Preferably, a composition according to the invention is provided in the form of a thin film. Advantageously, the film can be used as a dressing for a wound.

Preferably, the film thickness is in the range of about 5 μm to about 200 μm, more preferably about 20 μm to about 100 μm.

Advantageously, it has been found that a film according to the invention is robust, with strong handling properties and can be used as a dressing. Furthermore, a film according to the invention does not need to be removed by a patient. Instead, it is biodegradable. These advantages provide increased comfort for a user.

Preferably, the film of the invention can be produced in a multitude of geometries and dimensions to meet the needs for treatment of various shapes and sizes of wounds to different parts of the body of a patient.

Preferably, the film is transparent or translucent. This provides the advantage that in use the skin where the film is placed can be inspected.

Preferably, a composition of the invention is provided in the form of a film together with an additional support which is preferably a thin film. In this way, the invention provides an island dressing which comprises an island having a composition according to the invention surrounded by an additional supporting thin film.

Preferably, the additional supporting thin film is transparent or translucent. This provides the advantage that in use the skin where the film is placed can be inspected.

In a preferred embodiment, the additional supporting thin film is a polyurethane (PU) film.

Preferably, the additional supporting thin film is capable of providing peripheral adhesion to skin of a patient. In this regard, the additional supporting thin film preferably has adhesive applied to a body facing surface.

Preferably, the adhesive is acrylic based or silicone-based. More preferably, the adhesive is acrylic based.

Preferably, the adhesive is provided with at least one easy release liner which covers the adhesive on the body facing surface of the film until the film is ready for use. Just before use, the easy release liner can be peeled away from the body facing surface to expose the adhesive. This provides the advantage of protecting the adhesive and island dressing comprising collagen and honey until it is ready for use.

Preferably, the easy release liner comprises a tab which does not adhere to the adhesive. This provides the advantage that the tab can be easily gripped and facilitates removal of the easy-release liner to expose the adhesive.

Preferably, a composition or film according to the invention is sealed in a sachet prior to use. Preferably, the composition or film is sterile prior to use and the sachet has the advantage of protecting the composition or film. This mitigates the risk of infection for a user.

Consequently, the invention provides a package comprising a sealed sterile film dressing.

In a further aspect, the invention provides a method for production of a composition according to the invention which comprises the steps of preparing a collagen suspension, preparing a honey solution, adding the honey solution to the collagen suspension to provide a collagen and honey suspension.

Preferably, the collagen and honey suspension is subjected to the further steps of optionally degassing, and drying at low temperatures (preferably about 20° C. to about 35° C.) or at higher temperatures (preferably above about 35° C.) to provide a collagen and honey film.

In a preferred embodiment, the suspension is lyophilised or freeze-dried to form a porous sponge or membrane.

In a preferred embodiment, the composition is subjected to physical or chemical cross-linking. Advantageously, this imparts strength and other desirable properties to the film as required. The cross-linking method may include but is not limited to glutaraldehyde and other chemical cross-linking agents and dehydrothermal treatment.

Preferably, the collagen suspension is about a 0.5 wt % suspension.

Preferably it is prepared by hydrating about 2.5 g of type I bovine Achilles tendon collagen in about 500 ml of about 1 mM acid (preferably hydrochloric acid (HCl)) for about 24 hours and blending for about 5 hours. Once hydrated, the collagen is preferably transferred into a blender container, placed within an ice-filled Pyrex dish and blended. Preferably it is initially blended using a double-blade blender for about 2 hours, followed by blending with a homogeniser for a further about 3 hours, to produce a white collagen suspension.

Preferably, the honey solution has a concentration of from about 0.01 g/ml to about 0.2 g/ml. Preferably, the concentration is selected from the group consisting of about 0.2 g/ml, about 0.1 g/ml, about 0.05 g/ml, about 0.02 g/ml and about 0.01 g/ml.

Preferably, the honey solution is prepared by addition of honey of Unique Manuka Factor (UMF)+16 to distilled water. The highest honey content in the honey solution is preferably about 1.0 g/5 ml=about 0.2 g/ml.

Preferably, a syringe is used to transfer preferably about 5 g of honey into a flask preferably placed onto a weighing scale and preferably about 25 ml of distilled water is added. Preferably the mixture is stirred, preferably with a magnetic stirrer, preferably for at least about 1 hour. This preferably yields a solution comprising about 0.2 g/ml honey. Preferably, this solution was used to make up solutions having lower concentrations of honey by sequential dilution.

Preferably, the honey solution is added to the collagen suspension or vice versa. More preferably, a honey solution is added to a collagen suspension.

Preferably, a honey solution is added to the collagen suspension drop wise with continual homogenisation or added in bulk and then blended and/or homogenised.

Preferably, the resulting collagen-honey suspension is homogenised.

Preferably, the collagen-honey suspension is degassed, optionally in a vacuum oven, chamber or other facility to remove air bubbles.

Preferably, the suspension is then be poured into a mould, tray or on paper.

Preferably, the poured suspensions are then left to degas.

Preferably, the suspension is dried in an oven or chamber at low temperatures (about 20° C. to about 35° C.) or at higher temperatures (above about 35° C.) to produce a film.

Optionally, the suspension is lyophilised or freeze-dried to form porous sponges or membranes.

Preferably, the film is subjected to physical or chemical cross-linking to impart strength and other desirable properties to the film.

Preferably, the cross-linking method may include but is not limited to glutaraldehyde and optionally other chemical cross-linking agents and dehydrothermal treatment

BRIEF DESCRIPTION OF THE DRAWINGS

The invention will now be described by way of example with reference to the accompanying drawings, in which:—

DETAILED DESCRIPTION OF THE INVENTION

Figure 1:
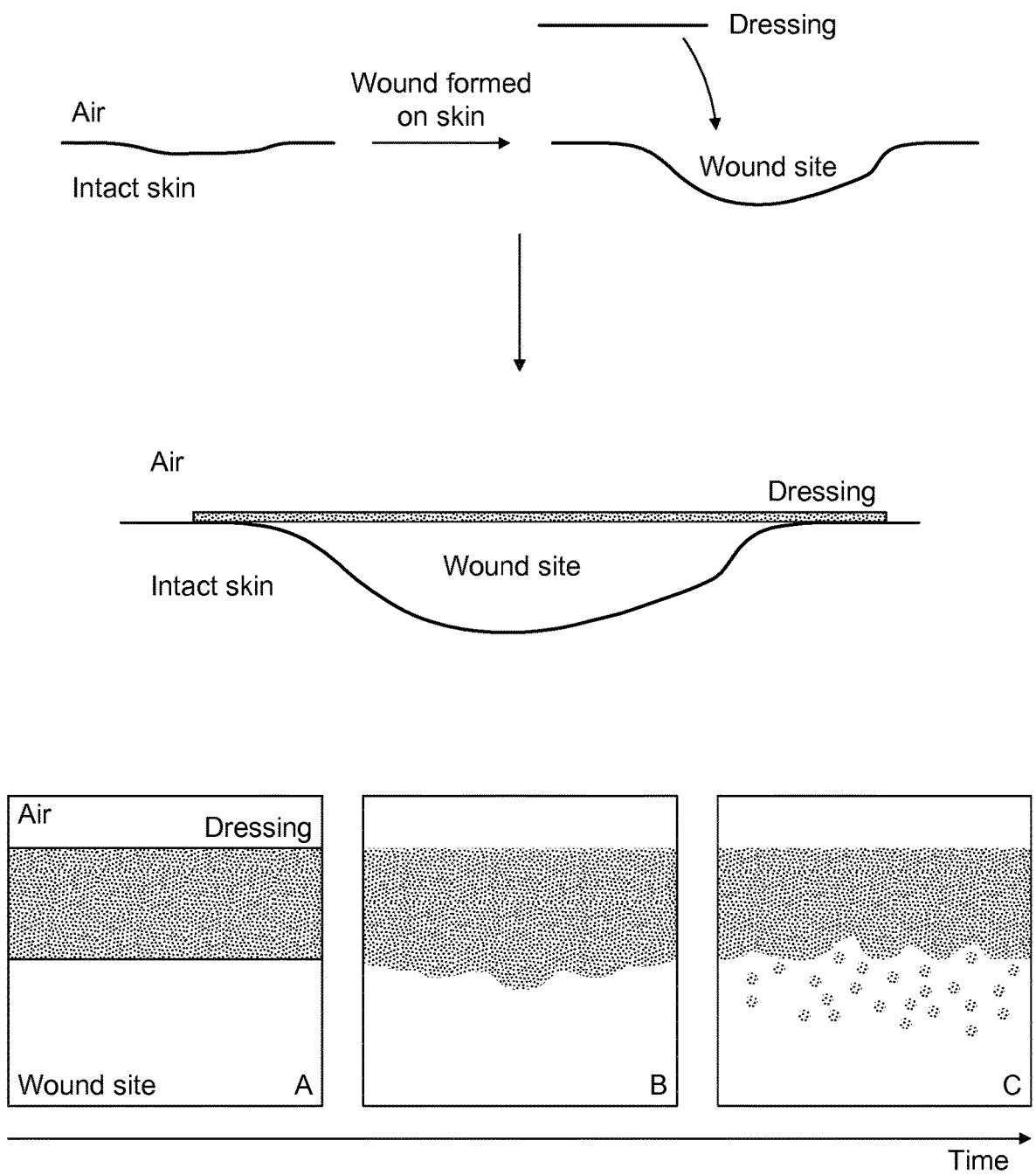
FIG. 1 shows a schematic diagram describing stages of wound treatment.

It will be appreciated that aspects, embodiments and preferred features of the invention have been described herein in a way that allows the specification to be written in a clear and concise way. However, it will be appreciated that the scope of the invention may include embodiments having combinations of all or some of the features described. Unless circumstances clearly dictate otherwise, aspects, embodiments and preferred features can be variously combined or separated in accordance with the invention. In a preferred embodiment, a composition in accordance with the invention comprises all aspects of the invention.

The word "about" is taken to mean optionally plus or minus 20%, more preferably optionally plus or minus 10%, even more preferably optionally plus or minus 5%, even more preferably optionally plus or minus 2.5%, most preferably optionally plus or minus 1%.

Within the context of this specification the word "comprises" is taken to mean "includes, among other things". It is not intended to be construed as "consists of only".

Within the context of this specification, the word "substantially" means preferably at least 90%, more preferably 95%, even more preferably 98%, most preferably 99%.

Within the context of this specification, "treatment" is taken to mean treatment of an existing condition or disease and/or prophylactic treatment in order to prevent incidence of a condition or disease. As such, the methods of the invention can be used for the treatment, prevention, inhibition of progression or delay in the onset of disease. "Treatment of a wound" is taken to mean reduction in the size or severity of the wound or the prevention or reduction of infection to the wound.

The term "wound" is taken to mean an injury in which skin is damaged, torn, cut, or punctured, or where blunt force trauma causes a contusion. It includes a sharp injury which damages the dermis of the skin or a burn which damages the skin.

Without being bound by theory, it is considered that collagen within a wound environment provides an alternative source of collagen (sacrificial substrate) that can be degraded by the high levels of MMPs (matrix metalloproteinases) allowing the endogenous collagen to continue normal wound healing. The collagen also finds roles in cellular signalling, differentiation, migration, angiogenesis and in the induction of growth factors to aid healing.

In addition, it is considered that in embodiments comprising honey, the honey in the composition may act to reduce water content, creating a more hostile environment for potential bacterial growth. Furthermore, the presence of honey leads to a low pH and this may serve to inhibit microbial growth while increasing oxygen diffusion and decreasing protease activity.

Matrix metalloproteinases (MMPs) play an integral part in the wound healing process. However, elevated levels of these MMPs break down healthy tissue and render wounds as non- or slow-healing. Furthermore, acidic pH has been shown to decrease protease activity and this may promoted by application of honey to induce lower wound pH levels during healing. This lower pH has also been shown to increase oxygen diffusion, another influential factor in wound healing, with this increase in oxygen availability also potentially promoting osmotic pressure induced by sugars in honey, which can act to reduce oedema.

As shown in table 1, both collagen alone and honey alone have previously been shown to have benefit in wound healing. In this regard, table 1 shows a summary of material properties and modality of action for collagen, honey and a novel combination of collagen and honey.

As shown in FIG. 1, the stages of wound treatment are as follows:
1—Dressing is placed on and around wound area
2—Collagen degrades and honey presents itself to the wound
3—Protease and collagenases break down collagen and further exposure of honey to the wound occurs
4—Anti-inflammatory and anti-bacterial activity of honey and biochemical action and cues of collagen facilitate wound healing
5—Regenerated epithelial layer formed with no toxic residues or synthetic particulates.

The figure shows a schematic illustrating application of a dressing over a wound bed and gradual breakdown and release of the components into the wound over time.

A: Sterile dressing is placed over the wound site forming a protective barrier. This may be covered and securely held in place by a secondary dressing or may form an island dressing.

B: as the dressing comes into contact with the wound site, the dressing components, namely collagen and honey, over time begin to interact with the wound. The honey may serve to lower pH, increase oxygen diffusion and decrease protease activity. The honey may also serve to create an osmotic pressure which can promote anti-inflammatory action and moist wound healing. The collagen will serve as a sacrificial substrate while also providing cues including those necessary for cellular differentiation, migration and angiogenesis.

C: over time the collagen begins to break down by the action of matrix metalloproteinases; this biodegradation makes the collagen particulates available in deeper wound site and neo-tissue forms to replace the collagen substrate. The honey continues also to serve as an antibacterial component throughout the healing process.

Compositions according to the invention were prepared as follows:

Materials and Methods

Collagen Suspension Preparation

A 0.5 wt % collagen suspension was prepared by hydrating 2.5 g of type I bovine Achilles tendon collagen. in 500 ml of 1 mM hydrochloric acid (HCl) for 24 hours and blending for 5 hours. Once hydrated, the collagen was transferred into a blender container, placed within an ice-filled Pyrex dish and blended initially using a double-blade blender for 2 hours, followed by blending with a homogeniser for a further 3 hours, to produce a white collagen suspension.

Honey Solution Preparation

Honey concentrations of 0.2, 0.1, 0.05, 0.02 and 0.01 g/ml in distilled water were prepared using honey of Unique Manuka Factor (UMF)+16. The highest honey content was 1.0 g/5 ml=0.2 g/ml (to achieve 25 ml, 5 g of honey was used). A syringe was used to transfer 5 g of honey into a 25 ml volumetric flask placed onto a weighing scale (Denver Instrument) and on filling of the volumetric flask with 25 ml of distilled water a magnetic stirrer was used to mix the solution for 1 hour. This yielded a 0.2 g/ml honey solution, which was used to make up solutions having the lower concentrations by sequential dilution.

Figure 2:
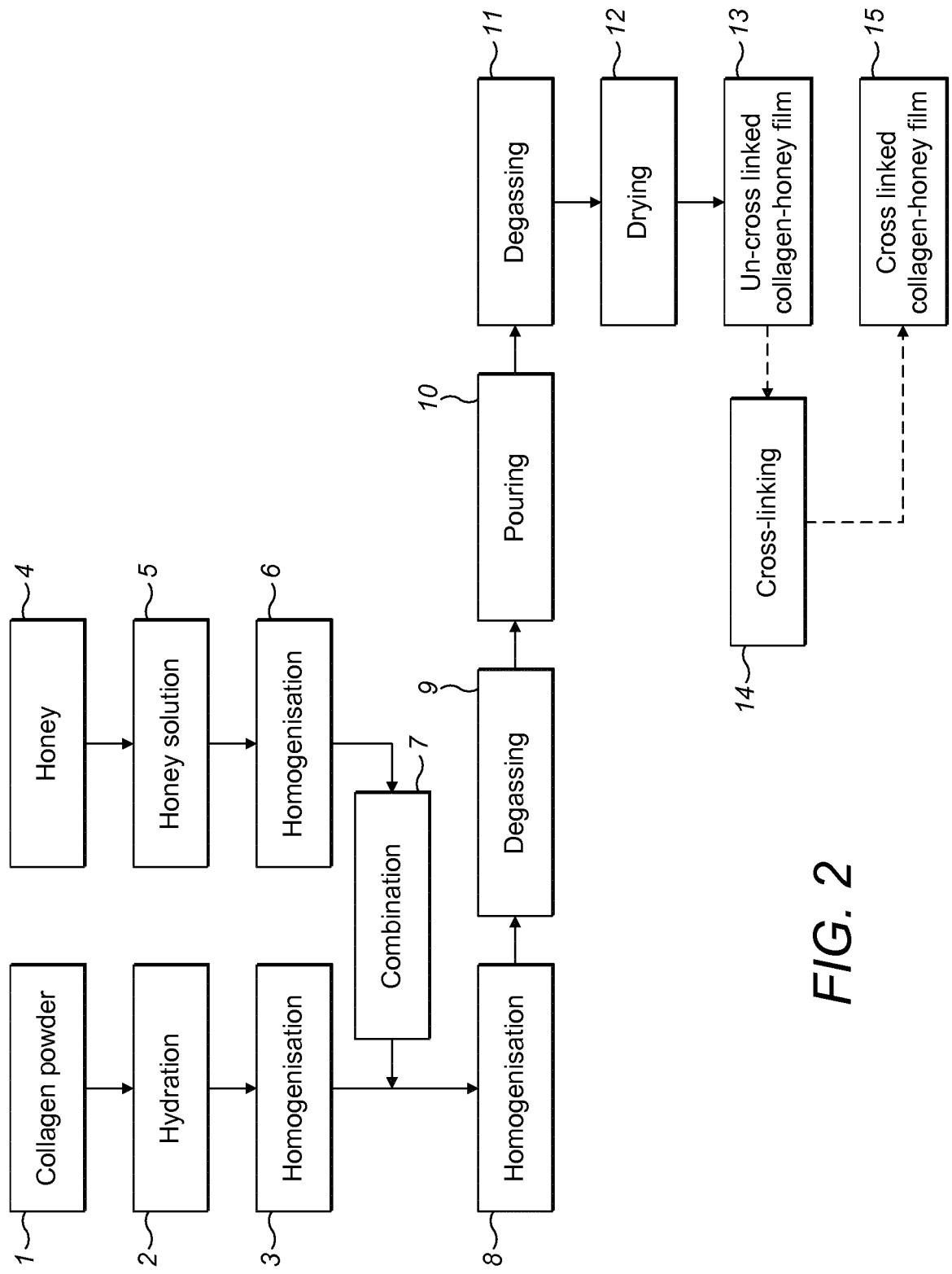
FIG. 2 shows a schematic diagram showing the stages in a method for production of a composition according to the invention.

As shown in FIG. 2, the method steps for production of compositions according to the invention were as follows:

(1) Lyophilised collagen may take the form of a powder, fibre, granules or other forms. The collagen may be type I, II, III, IV or other. It may be purchased pre-prepared or may be extracted from cartilage. The collagen may also be of a denatured form such as gelatin.

(2) The collagen may be hydrated in hydrochloric acid, acetic acid or any other acidic solution at pH<7. The duration of hydration may vary according to quantity of collagen and contact area between the solute and solvent. This hydration may typically take between 2 hours and 24 hours. The hydrating collagen should be left refrigerated.

(3) The hydrated collagen was homogenised as described above, using a blender and/or homogeniser. Blending time depended on collagen weight fraction and volumes. The blending solution was kept cool and this may be achieved using an ice-bath to surround it.

(4) Honey which may take the form of a viscous or semi-viscous liquid or powder can be used. The honey may be sourced from the *Leptospermum Scoparium* bush, indigenous to New Zealand, which has shown to exhibit unique antibacterial and anti-inflammatory properties and to promote wound healing. The honey may also be from different sources and may exhibit varying degrees of bioactivity.

(5) A honey solution was made up as described above using distilled water in order to aid accurate transfer of specific honey quantities.

(6) The honey solution was homogenised using a blender and or homogeniser and a magnetic stirrer may also be used. Physical agitation, by shaking, may also be used.

(7) The honey solution was added to the homogenised collagen suspension using a pipette. The honey solution was transferred drop-wise with continual homogenisation or it was added in bulk and then blended and/or homogenised.

(8) The resulting collagen-honey suspension can be homogenised.

(9) The resulting collagen-honey suspension was degassed in a vacuum oven, chamber or other facility to remove air bubbles.

(10) The collagen and honey suspension was poured using a pipette into a mould, tray or onto paper.

(11) The poured suspensions were left to degas

(12) The suspensions were dried in an oven or chamber at low temperatures (about 20° C. to about 35° C.) or at higher temperatures (above about 35° C.). The suspension was also lyophilised or freeze-dried to form porous sponges or membranes.

(13) The resulting composition comprising collagen and honey in the form of a film was provided

(14) Physical or chemical cross-linking may be used to impart strength and/or other desirable properties to the film as required. The cross-linking method may include but is not limited to treatment with glutaraldehyde and/or other chemical cross-linking agents and optionally dehydrothermal treatment.

Results

Compositions according to the invention were prepared as described above. The collagen and honey weight percentages and ratios of six thin films, fabricated under the same conditions are shown in Table 2.

Each film identified in Table 2 was fabricated using 20 ml of collagen and honey suspension and dried in a vacuum oven for four days under a temperature of 30° C. at ambient pressure.

TABLE 2

| | Collagen:Honey Ratio | | | | | |
|---|---|---|---|---|---|---|
| | Control 1:0<br>1 | 5:1<br>2 | 5:2<br>3 | 1:1<br>4 | 1:2<br>5 | 1:4<br>6 |
| Collagen wt. % (weight in grams/50 ml) | 0.45 (0.25 g) | 0.45 (0.25 g) | 0.45 (0.25 g) | 0.45 (0.25 g) | 0.45 (0.25 g) | 0.45 (0.25 g) |
| Honey wt. % (weight in grams/50 ml) | 0 | 0.09 (0.05 g) | 0.18 (0.1 g) | 0.45 (0.25 g) | 0.9 (0.5 g) | 1.8 (1.0 g) |
| Description | A thin, highly transparent and homogenous clear film. No air bubbles. | A thin transparent and homogenous near clear film with little surface irregularity and a single air bubble. | A translucent film with yellow tint and small dispersed agglomeration. | A translucent film with yellow tint and small dispersed agglomeration. Material exhibits adhesive properties and more difficult to remove from mould. | A translucent film with yellow tint and adhesive behaviour. Material is difficult to remove from mould. | A translucent and adhesive film with good surface homogeneity. Material feels less brittle compared with sample 1 (control) |

Figure 3:
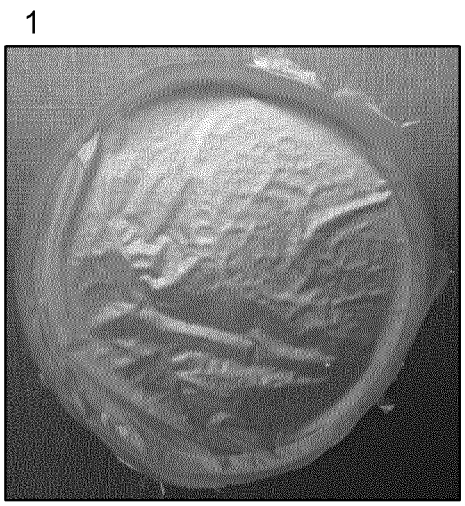
FIG. 3 shows photographs of films having compositions according to the invention.
Figure 3:
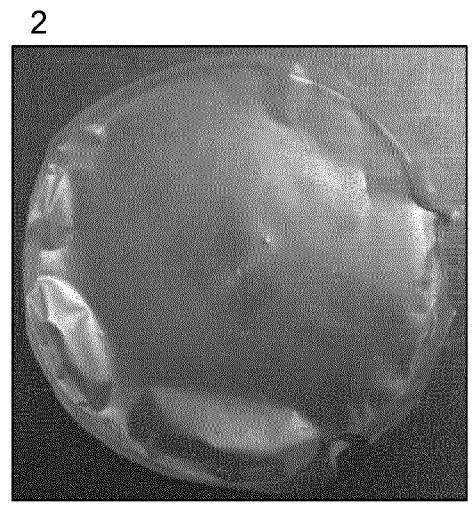
Figure 3:
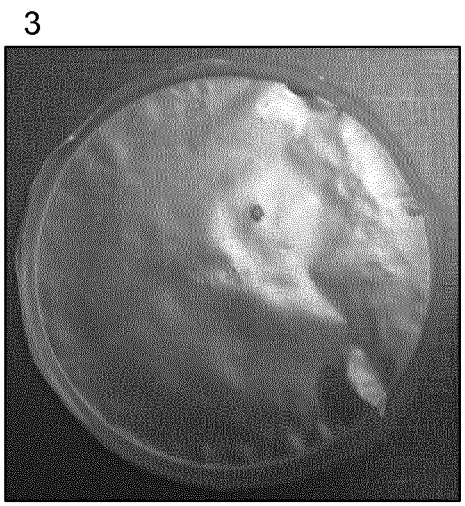
Figure 3:
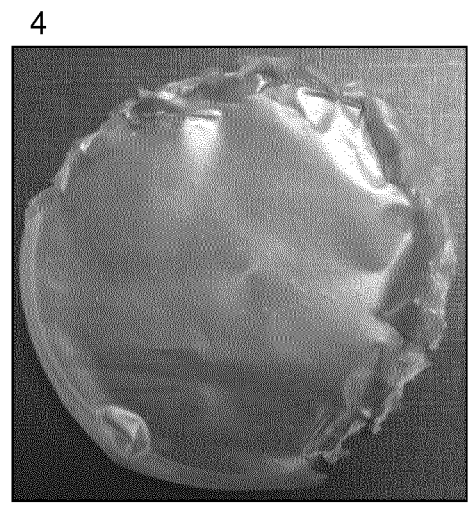
Figure 3:
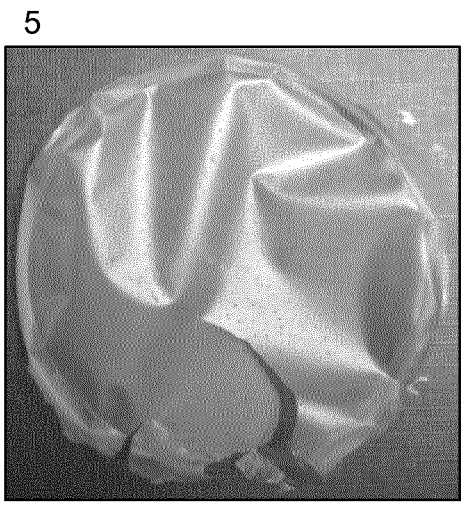
Figure 3:
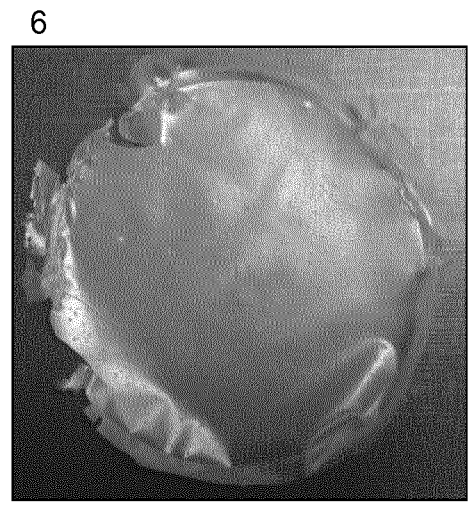

Films having various compositions identified in Table 2 were prepared in accordance with the invention and they are shown in FIG. 3. The films were compared and comparative test data shows that:

The control scaffold appeared consistent with previously fabricated films under the same conditions The transparency of the composition decreased with increasing honey content There was increased adhesion of films comprising compositions according to the invention with a Teflon mould and associated difficulty in removal of the compositions from the mould with the addition of honey The films with honey were felt to be more robust than the control film The above described embodiments have been given by way of example only, and the skilled reader will naturally appreciate that many variations could be made thereto without departing from the scope of the claims.

The invention claimed is:

1. A free-standing, biodegradable honey and collagen film produced from a dried aqueous suspension, the aqueous suspension comprising 0.1% to 2.0% bovine collagen by weight and 0.05% to 5.0% honey of Unique Manuka Factor (UMF)+16 by weight;
wherein the free-standing, biodegradable honey and collagen film comprises substantially bovine collagen, honey of UMF+16, and water suitable for the treatment of a wound.

2. The free-standing, biodegradable honey and collagen film of claim 1 wherein the wound is inflicted by a burn.

3. The free-standing, biodegradable honey and collagen film of claim 1, wherein the composition further comprises one or more additional medicaments for the treatment of a wound.

4. The free-standing, biodegradable honey and collagen film of claim 1, wherein the free-standing, biodegradable honey and collagen film:
(a) has a thickness in the range of 5 μm to 2 μm; or
(b) is transparent or translucent; or
c) has a thickness in the range of 5 μm to 200 μm and is transparent or translucent.

5. An island dressing comprising the free-standing, biodegradable honey and collagen film of claim 1, wherein the composition is surrounded by an additional supporting thin film.

6. The island dressing of claim 5, wherein the additional supporting thin film:
(a) is transparent or translucent; or
(b) is a polyurethane (PU) film; or
(c) is transparent PU film or translucent PU film.

7. The island dressing of claim 5, wherein the additional supporting thin film has adhesive applied to a body facing surface and provides peripheral adhesion to skin of a patient.

8. The island dressing of claim 7, Wherein the adhesive is acrylic based or silicone-based.

9. The island dressing of claim 7 wherein the adhesive is provided with at least one release liner which covers the adhesive on the body facing surface of the film until the film is ready tier use, and wherein the release liner optionally comprises a tab which does not adhere to the adhesive.

10. The free-standing, biodegradable honey and collagen film of claim 1, wherein the aqueous suspension comprises 0.5% to 1.0% bovine collagen by weight and 0,18% to 1.8% honey of UMF+16 by weight.

11. The free-standing, biodegradable honey and collagen film of claim 1, wherein the aqueous suspension comprises 0.5% to 1.0% bovine collagen by weight and 0.45% to 0.9% honey of UMF..16 by weight.

12. The free-standing, biodegradable honey and collagen film of claim 1, consisting essentially of bovine collagen, honey of UMF+16, and water.

13. The free-standing, biodegradable honey and collagen film of claim 1, consisting essentially of bovine collagen, honey of UMF+16, water, and an additional medicament.

14. The free-standing, biodegradable honey and collagen film of claim 1, consisting of bovine collagen, honey of UMF+16, and water.

15. A method for production of a free-standing, biodegradable honey and collagen film, the method comprising
(a) preparing. a bovine collagen suspension,
(b) homogenizing the collagen suspension,
(c) preparing a honey solution, wherein the honey is of Unique Manuka Factor (UMF)+16, and
(d) adding the honey solution to the collagen suspension to provide a collagen and honey suspension, wherein the collagen and honey suspension comprises 0.1% to 2.0% bovine collagen by weight and 0.05% to 5.0% honey by weight;
(e) homogenizing or blending the collagen and honey suspension, and
(f) drying the collagen and honey suspension to provide a free-standing, biodegradable honey and collagen film comprising substantially bovine collagen, honey of UMF+16, and water suitable for the treatment of a wound.

16. The method of claim 15, further comprising physically cross-linking or chemically cross-linking the free-standing, biodegradable honey and collagen film.

17. The method of claim 15, further comprising administering the free-standing, biodegradable honey and collagen film topically to a wound on the skin of a patient thereby treating the wound.

18. The method of claim 17 wherein the free-standing, biodegradable honey and collagen film is applied to the wound for about 2 to about 7 days and then reapplied depending on the severity of the wound until the wound is healed.

19. The method of claim 15, wherein the collagen and honey suspension. comprises 0.5% to 1.0% bovine collagen by weight and 0.18% to 1.8% honey by weight.

20. The method of claim 15, wherein the collagen and honey suspension. comprises 0.5% to 1.0% bovine collagen by weight and 0.45% to 0.9% honey by weight.

* * * * *